United States Patent [19]

Neeley

[11] Patent Number: 5,166,498
[45] Date of Patent: Nov. 24, 1992

[54] PROCEDURE AND ASSEMBLY FOR DRAWING BLOOD

[76] Inventor: William E. Neeley, 22 High View Rd., Madison, Conn. 06443

[21] Appl. No.: 844,926

[22] Filed: Mar. 4, 1992

Related U.S. Application Data

[63] Continuation of Ser. No. 710,403, Jun. 5, 1991, abandoned, which is a continuation of Ser. No. 410,144, Sep. 20, 1989, abandoned.

[51] Int. Cl.$^5$ .......................... G06F 15/20; G06K 7/10
[52] U.S. Cl. .................................. 235/375; 235/462; 235/472; 364/413.01
[58] Field of Search ............... 235/375, 449, 472, 462; 364/413.01, 413.03, 567

[56] References Cited

U.S. PATENT DOCUMENTS

| | | | |
|---|---|---|---|
| 3,831,006 | 8/1974 | Chaffin et al. | 235/375 |
| 3,848,112 | 11/1974 | Weichselbaum et al. | 235/375 |
| 4,164,320 | 8/1979 | Irazoqui et al. | 235/449 |
| 4,476,381 | 10/1984 | Rubin | 235/375 |
| 4,628,193 | 12/1986 | Blum | 235/375 |
| 4,706,095 | 11/1987 | Ouo et al. | 235/487 |
| 4,706,096 | 11/1987 | Sato | 235/487 |
| 4,734,710 | 3/1988 | Sato et al. | 235/487 |
| 4,746,932 | 5/1988 | Sato | 234/385 |
| 4,835,372 | 5/1989 | Gombrich et al. | 235/375 |
| 4,853,521 | 8/1989 | Claeys et al. | 235/472 |

Primary Examiner—Eugene R. LaRoche
Assistant Examiner—Christopher R. Glembocki
Attorney, Agent, or Firm—William W. Jones

[57] ABSTRACT

Patients in hospitals are pvovided with identification bracelets which display the patient identity number in a machine-readable form, such as a bar code. Blood or other samples are taken from patients by a technician, nurse, or the like who carries a microprocessor-operated device for optically scanning the identification bracelet-coded patient identifications. When the patient ID is read, the device automatically prints out a label for securement to the specimen tube. The label includes the patient's name; ID number; tests to be performed on the specimen sample; and the time and date the sample was drawn. The device is preferably housed in the tray which carries the sample tubes and sampling needles. A connection can be made between a mainframe computer and the device's microprocessor so that the device can confirm to the mainframe computer that all of the samples were drawn, and so that the mainframe computer can preprogram the device to prepare for the next round of specimen samples.

3 Claims, 2 Drawing Sheets

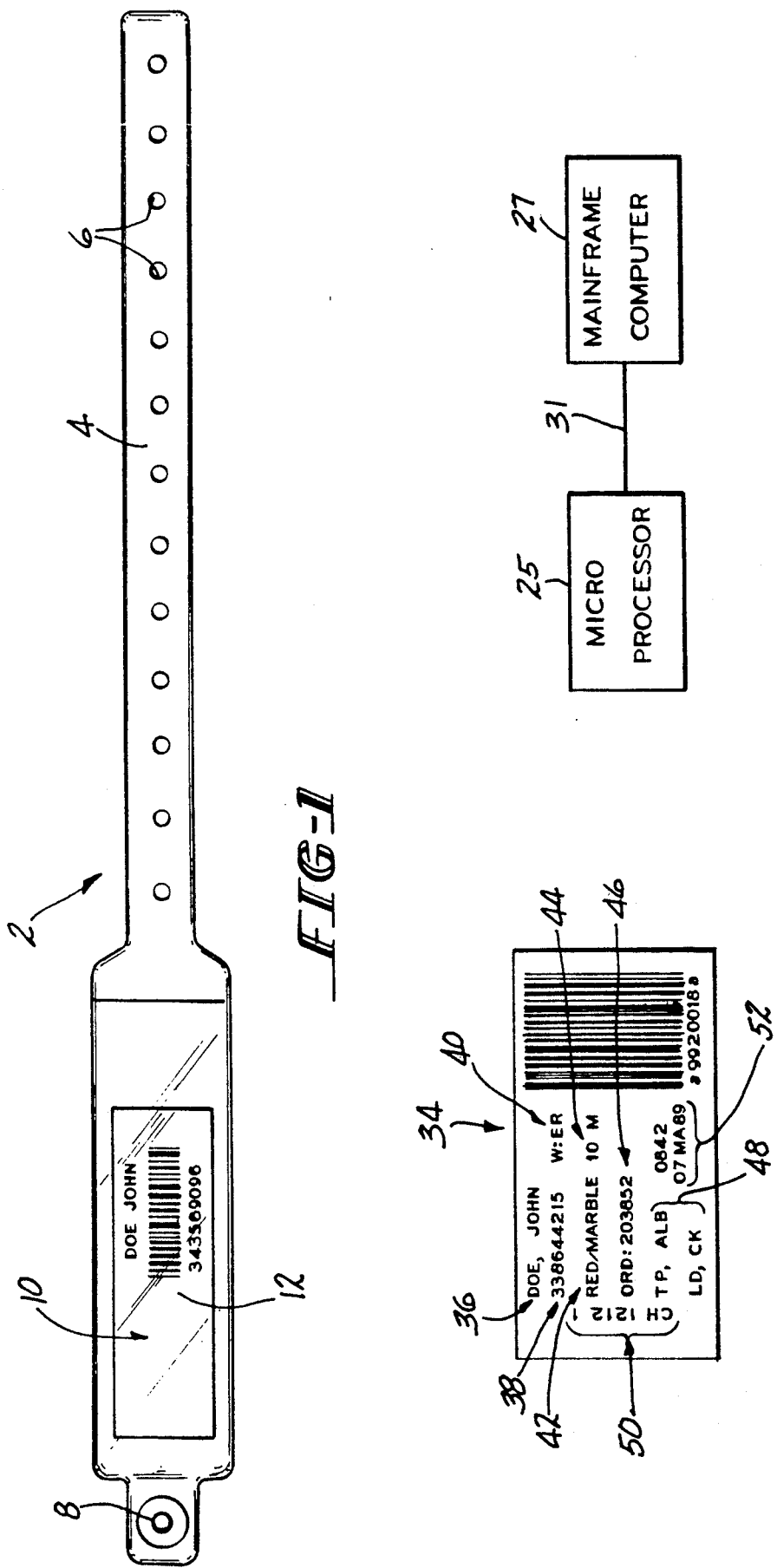

PROCEDURE AND ASSEMBLY FOR DRAWING BLOOD

This is a continuation of copending application Ser. No. 07/710,403 filed Jun. 5, 1991, now abandoned which in turn is a continuation of Ser. No. 07/410,144 filed Sep. 20, 1989, now abandoned.

This invention relates to a procedure and equipment for drawing specimen samples from hospital patients. More particularly, this invention ensures that the correct patient information is displayed on the labels attached to the specimen-containing tubes.

Blood and other patient specimen samples are taken in hospitals by hospital employees who go through the hospital wards with a specimen tray which holds a plurality of specimen tubes, needles, and the like paraphenalia. The employee will have a list of patients who require samples to be taken. The list may be in the form of preprinted labels which display the name of the patient, the patient's hospital ID number, and the tests to be performed on the specimen sample. There is preferably a place on the label where the person taking the sample can write down the time the sample was taken.

Each patient in the hospital will be given a plastic or the like ID bracelet to be worn while hospitalized. The bracelet displays the patient's name and hospital ID number. The hospital ID number is a number which is assigned to the patient for the purpose of keeping accurate records in the hospital as to tests, procedures, billings, and the like. The patient ID number may be the patient's social security number or the like. In some cases, plastic embossed ID cards, similar to charge cards, may be used and slipped into a pocket in the bracelet. When samples are taken from the patient, the ID card will be removed from the bracelet and used to print information on the specimen label. The ID card is then returned to the patient's bracelet pocket.

It will be appreciated that potential for problems and errors resides in the aforesaid procedures for taking samples from hospital patients. The reliability of these procedures is heavily dependent on the reliability of the person doing the sampling. When the list of patients to be sampled is in the form of a preprinted strip of labels, the sampler must match up the patient from the ID bracelet with the preprinted label. Thus a certain order of sampling may be indicated. Moving patients from room to room can complicate the taking of the samples, or render it time consuming. Commonality of patient names can confuse the sampler. Close comparison of the patient bracelet ID number and the label ID number will be necessary. The exact time of the sampling is desirable information but is not always accurately written on the label by the sampler. The presence of a large number of preprinted labels in the sampling tray can create a possibility of the wrong label being placed on one's specimen tube. This invention relates to an improved procedure for taking blood samples, or the like, from patients in a hospital or similar environment. The invention involves the use of patient ID bracelets which have machine readable patient identification numbers printed thereon. The identification numbers can take the form of a bar code or the like. A label printer is used by the person taking the sample. The label printer is actuated by a scanner which is used to scan the patient ID bracelet. The label printer includes a microprocessor which has stored patient information in it. Once the ID bracelet is scanned, the microprocessor knows which patient is being attended, and the microprocessor directs the printer to print a label with the correct patient ID number; the patient's name; and the tests to be performed on the sample being taken from the patient. The microprocessor will also include an onboard clock whereby the correct time of taking the sample will be printed on the label. The attendant then need merely adhere the printed label to the tube holding the patient's specimen, and proceed to the next patient. The microprocessor and label printer are preferably incorporated into the specimen tube tray for the convenience and ease of use of the attendant. The microprocessor will preferably be provided with a connection which will enable direct communication between the microprocessor and the hospital or laboratory mainframe computer. Thus the mainframe computer can program the patient information into the tray microprocesor for the upcoming sample collecting round. After the samples have been collected, the tray microprocessor can confirm the samples having been taken to the mainframe.

It is therefore an object of this invention to provide an improved procedure for taking patient samples in a hospital, or the like, environment.

It is a further object of this invention to provide an improved procedure of the character described which substantially eliminates the chances of improperly labeling the specimen sample.

It is an additional object of this invention to provide an improved procedure of the character described wherein the sample labels are printed at the time of taking the specimens.

It is another object of this invention to provide an improved procedure of the character described wherein information for the specimen sample labels is produced by scanning machine-readable indicia on a patient's hospital ID bracelet thereby triggering a microprocessor onboard the specimen tray.

These and other objects and advantages of the invention will become more readily apparent from the following detailed description of a preferred embodiment thereof when taken in conjunction with the accompanying drawings in which:

FIG. 1 is a plan view of a hospital patient identification bracelet adapted for use in practicing this invention;

FIG. 2 is plan view of a sample specimen bottle label printed by the device of this invention;

FIG. 4 is a schematic illustration of the connection between the tray microprocessor and the hospital mainframe computer.

Figure 3:
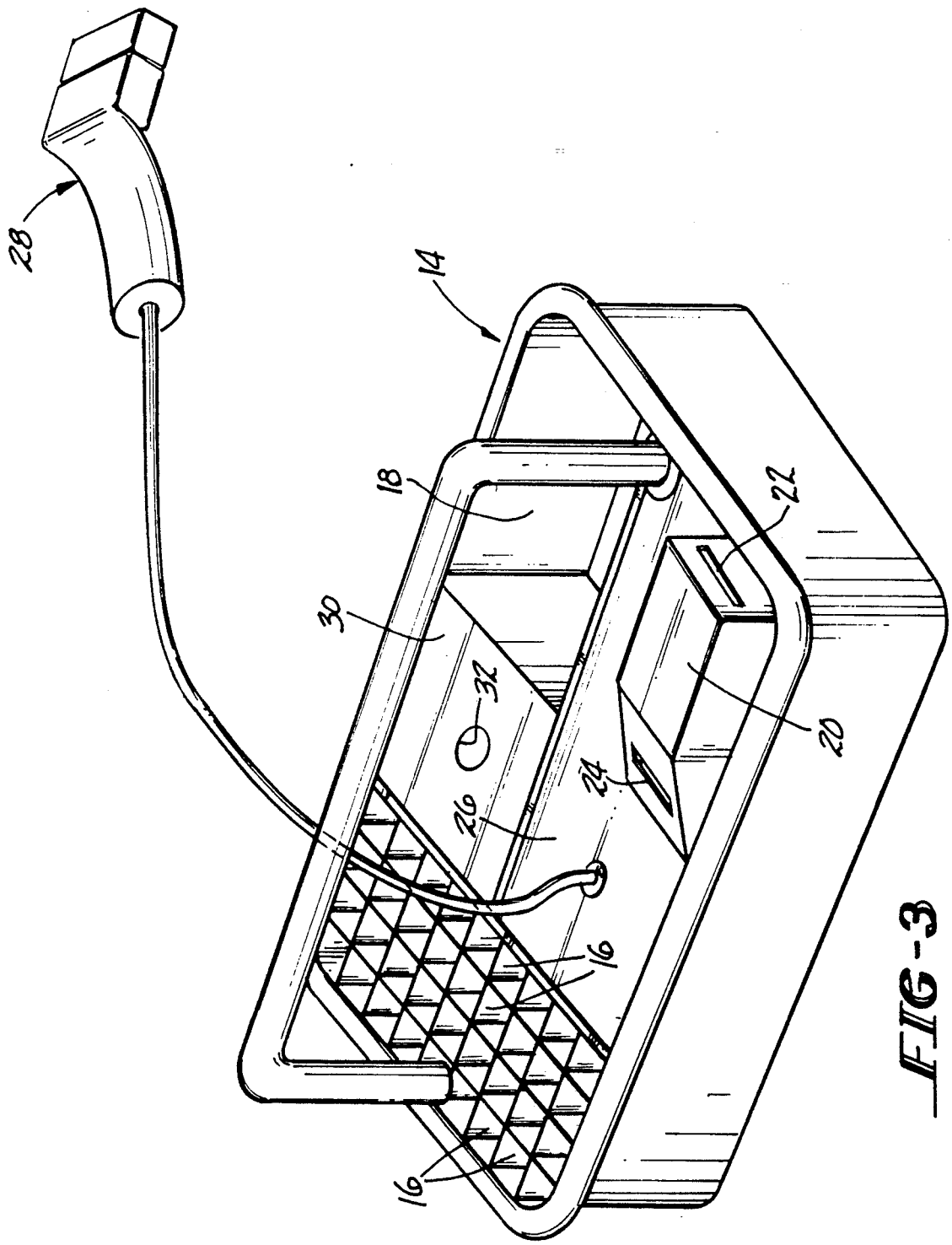
FIG. 3 is a perspective view of a blood sample tray-printer assembly embodying this invention.

Referring now to FIG. 1, there is shown a conventional hospital patient ID bracelet 2 which includes a strap portion 4 having serial apertures 6 for receiving a snap fastener 8 on the end of the bracelet 2. A pocket pouch 10 on the bracelet receives a patient identification slip or tag 12 having the patient's name printed on it, and having the patient's hospital identification number printed on it both in Arabic numerals and also in a machine-readable form such as a bar code. All of the patient's records in the hospital will be catalogued and identified by the hospital identification number.

Referring to FIGS. 2 and 3, there is shown in FIG. 3 a blood sampling tray which has been adapted to operate in accordance with this invention. The tray 14 includes a portion thereof which is divided into a plurality of cells 16 in which the specimen sampling bottles or tubes are disposed. A well 18 is provided to hold a needle discard recepticle (not shown). A label printer 20 is built into the tray 14, or may be removably mounted therein. The printed labels are ejected from the printer 20 via slot 22, and the removable backing for the individual labels is ejected from the printer 20 via slot 24. It will be understood that the label printer 20 is preloaded with a roll of blank labels which are precoated with an adhesive covered by a removable non-adhering strip of material, such as waxed paper, or the like. The printer 20 is controlled by a microprocessor housed in the tray 14 in the compartment 26. A hand held bar code scanner 28 is operably connected to the printer microprocessor. The scanner 28 is preferably a laser or charge coupled diode array scanner which is adapted to read the patient's ID bracelet which, due to the fact that it is worn on an irregular surface, I.E. one's wrist, is difficult for a conventional wand scanner to read. Interfacing the scanner 28 with the microprocessor allows the microprocessor to identify the patient and activate the printer to print the proper label information. A battery power pack is disposed in the tray compartment 30 for powering the scanner, microprocessor and printer. The power pack may be rechargeable. A port 32 is provided for recharging the power pack. The port 32 also is provided with an interface for the tray microprocessor. This interface is used for the intercommunication between the tray microprocessor and the hospital or laboratory mainframe computer, as shown in FIG. 4 wherein the tray microprocessor is denoted by the numeral 25, the mainframe computer by the numeral 27 and the interface connection by the numeral 31. The hospital computer 27 can thus program the tray microprocessor 25 as to which patients are to be sampled and what tests are to be performed on the samples taken from the respective patients. Additionally, the tray microprocessor 25 can confirm to the mainframe computer 27, after the samples are taken, that the sampling instructions were carried out.

FIG. 2 shows a typical specimen tube label 34 produced by the printer 20 after the ID bracelet tag 12 is scanned. The label 34 displays the patient's name 36; ID number 38; the patient ward location 40; the tube type 42; the specimen volume 44; the patient order number 46; the tests to be performed 48; the patient test accession number 50; and the time and date the specimen is drawn 52.

It will be readily appreciated that this invention provides for safer, more accurate, specimen sampling of patients. The microprocessor label printer may be obtained from Pitney Bowes Corporation. The ID bracelet scanner can be obtained from Opticon, Inc. While the invention has been described in connection with the taking of blood samples from hospital patients, it will be readily appreciated that it can be used in connection with other specimen sampling of patients in other environs, such as clinics, physician's offices, sanitariums, or the like. Likewise, the invention can be performed with other forms of machine readable means, such as a magnetically coded bracelet which can be scanned by a magnetic scanner. The invention allows the person who draws the samples to become less involved in the reliability of the sampling. Since many changes and variations of the disclosed embodiment of the invention may be made without departing from the inventive concept, it is not intended to limit the invention otherwise than as required by the appended claims.

What is claimed is:

1. A method for taking specimen samples from patients, said method comprising the steps of:
   a) providing a portable device having the following components: an onboard printer; an onboard computer containing stored patient identification information and specimen sample testing instructions keyed to said patient identification information; an onboard supply of blank labels for said printer to print information on; and an onboard scanner means operably connected to said computer, for transmitting patient identity information of said computer; all of said components being housed in a single portable container;
   b) providing a patient tag having disposed thereon machine readable indicia containing said patient identity information which identifies the patient to whom the tag was issued;
   c) scanning said machine readable indicia at the time the specimen sample is taken to transmit said patient identity information to said onboard computer;
   d) creating a specimen sample container label by printing with said printer the patient identification information and the specimen sample test instructions on a blank label taken from said supply thereof, said identification information and test instructions being keyed to the patient identity information input from said scanning step; said supply of blank labels providing the primary source of specimen sample container labels for affixation to specimen sample containers; and
   e) attaching said printed specimen sample container label to a specimen sample container for the first time at the time the patient specimen is taken.

2. The method of claim 1 wherein said supply of blank labels is the sole source of specimen sample container labels.

3. The method of claim 2 comprising the further step of printing on the label the time and date on which the label is created.

* * * * *